(12) United States Patent
Delage et al.

(10) Patent No.: US 6,755,860 B2
(45) Date of Patent: Jun. 29, 2004

(54) INTRAOCULAR LENSES TO CORRECT APHAKIA

(75) Inventors: Denis Delage, Yevre le Chatel (FR); Renato Liffredo, Parabiago (IT)

(73) Assignee: Biotech, Pithiviers (FR)

( * ) Notice: Subject to any disclaimer, the term of this patent is extended or adjusted under 35 U.S.C. 154(b) by 0 days.

(21) Appl. No.: 09/968,711

(22) Filed: Oct. 2, 2001

(65) Prior Publication Data

US 2003/0065388 A1 Apr. 3, 2003

(30) Foreign Application Priority Data

Oct. 2, 2000 (FR) .............................................. 00 12531

(51) Int. Cl.[7] .................................................. A61F 2/16
(52) U.S. Cl. ...................................... 623/6.51; 623/6.49
(58) Field of Search ...................... 623/6.11, 6.38–6.55, 623/FOR 105

(56) References Cited

U.S. PATENT DOCUMENTS 4,657,546 A   4/1987  Shearing 6,461,384 B1 * 10/2002  Hoffmann et al. ......... 623/6.51

OTHER PUBLICATIONS

Stamper et al., Intraocular Lens Data, Ophthalmology—Instrument and Book Supplement 1984, pp. 179–180.*

* cited by examiner

*Primary Examiner*—David H. Willse
(74) *Attorney, Agent, or Firm*—Lowe Hauptman Gilman & Berner, LLP

(57) ABSTRACT

An intraocular lens includes: a substantially disk-shaped optical portion; a support portion having two closed pairs of haptic portions arranged symmetrically about a first diameter of the optical portion, each pair of the haptic portions being symmetrical with each other about a second diameter of the optical portion, the second diameter of the optical portion being substantially perpendicular to the first diameter of the optical portion. Each haptic portion has two side segments, each of the side segments having a first end fixed to a periphery of the optical portion and a second end fixed to a contact portion joining the two side segments.

18 Claims, 3 Drawing Sheets

INTRAOCULAR LENSES TO CORRECT APHAKIA

BACKGROUND OF THE INVENTION

This invention relates to an intraocular lens designed to be inserted in a capsular sac in an eye.

Intraocular lenses are designed to correct aphakia during an operation for a cataract. A cataract is characterized by the progressive loss of vision because the cornea in the patient's eye becomes opaque. A surgical operation is performed to extract the opacified cornea and to replace it with an artificial cornea called an intraocular lens. The intraocular lens may be placed in the anterior chamber in front of the iris or in the posterior chamber behind the iris, in a ciliary seat or in the capsular sac of the eye. The lens is composed of two parts, an optical part enabling vision that may be single-focal or multi-focal, and a support or haptic portion that will interact with the tissues by mechanical thrust and cellular growth and hold the lens in position in the eye. There are two types of implants used to replace the natural cornea at the present time, namely "rigid" implants and "flexible" implants.

Polymethylmethacrylate (PMMA) is usually used for rigid intraocular lenses. The flexible implant can bend and be inserted through a very small cornean or scleral incision about 3 millimeters long, after extraction of the natural lens nucleus from the capsular sac. This technique reduces residual astigmatism. Many intraocular lenses made of flexible material have already been proposed. For example, these lenses may be made from polysiloxanes, or flexible hydrophobic or hydrophilic acrylic polymers (copolyhema). Intraocular lenses made of co-polyhema are made by machining in the dry state, and the material will then be hydrated to make it flexible.

A flexible single piece intraocular lens disclosed in French Patent Application FR 2 766 699, is designed to prevent movement of the lens optics along the optical axis when the lens is being put into place. This lens is shown in FIG. 4. In order to achieve this purpose, closed haptic portions 410 having legs 411, 412 that are not radial are used. Thus, in theory, forces transmitted through the legs 411, 412 onto the optical part 401 when the lens is in position in the capsular sac of the eye do not have a radial component. Consequently, the optical part 401 should not move or be deformed. However, note that according to FIG. 4, the longitudinal axes of the legs 411, 412 for each haptic portion 410 intersect at a point S' that is in the angular section with center O and with an arc defined by the contact portion 414 of the haptic portion joining the free ends of the legs 411, 412. Once the lens is in position, centripetal forces will be applied to each haptic portion 410. Considering the geometry of each haptic portion defined above, these forces will induce a rotation moment on each leg 411, 412. According to FIG. 4, these two rotation moments will have opposite signs. If the values of these two moments are the same, then the haptic portion will simply be compressed, which will necessarily cause buckling of legs. If the sum of the moments is not zero, the leg with the smallest moment will be compressed and the haptic portion will pivot towards the direction of the highest moment. Thus, in all cases, at least one leg will be compressed. This compression phenomenon is also illustrated in FIG. 5a in which the shape of a hapic portion as illustrated in FIG. 4 is shown. In this figure, the compression C exerted on the haptic portion when the lens is in position causes a centripetal component Fc1 and a tangential component Ft1 to be applied to each leg 411, 412.

Due to the particular geometry of the haptic portion of the lens, the signs of these tangential components Ft1 are opposite and are in opposite directions. Depending on the value of these forces, the phenomena described above will be applied to each leg 411, 412. These phenomena will generate an accumulation of stresses that will result either in random deformation of the leg(s) causing instability in the position of the optical part, or an additional pressure exerted on the peripheral tissues of the capsular sac that can cause complications for the patient. These phenomena may also occur when the geometry of each haptic portion is such that the two legs are facing inwards instead of outwards as shown in FIG. 5b. In this case, the tangential components Ft2 will be towards each other.

SUMMARY OF THE INVENTION

The purpose of this invention is to overcome the disadvantages of prior art by proposing an intraocular lens in which the haptic portions do not cause any displacement of the optical part along the optical axis, or stress accumulation on the optical part or on the peripheral tissues.

This objective is achieved by an intraocular lens comprising an optical part approximately in the shape of a disk and a support part or haptic portion comprising two closed pairs of haptic portions laid out symmetrically about a first diameter of the optical part, the haptic portions in each pair being symmetrical with each other about a second diameter approximately perpendicular to the first diameter, characterized in that each haptic portion is provided with two arms or side segments in which a first end is fixed to the periphery of the optical part and, for each haptic portion, the longitudinal axes of the side segments intersect at a point that is not included in an angular sector with the same center as the optical center of the optical part, and in which the arc consists of a contact portion joining the second ends of the side segments of the same haptic portion.

BRIEF DESCRIPTION OF THE DRAWINGS

The invention and its characteristics and advantages will be more clearly understandable after reading the description with reference to the attached drawings in which.

DETAILED DESCRIPTION

The technical context and problems encountered with known lenses will be summarized briefly before going on to describe the invention. Flexible intraocular lenses that did not use an open shaped haptic portion used another shape called a shuttle, particularly suitable for introduction by injector. This model can be deformed by buckling, pushing the optic towards the back capsule, or by local deformation at the end.

Subsequently, designs were varied in quadripod or tripod form with perforated or non-perforated haptic portions.

Figure 4:
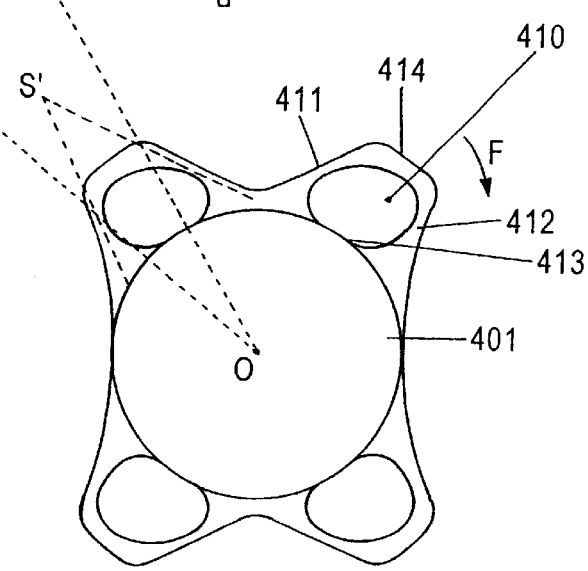
FIG. 4 is a view of a flexible single piece intraocular lens according to the Prior Art.
Figure 5A:
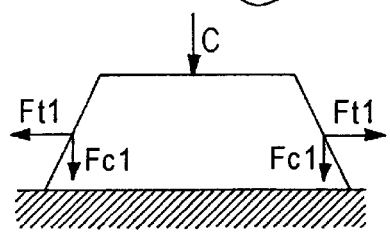
FIGS. 5a–5b and 6a–6c diagrammatically show compression forces applicable to a haptic portion when the lens is in place in the capsular sac, for different haptic portion geometries.
Figure 5B:
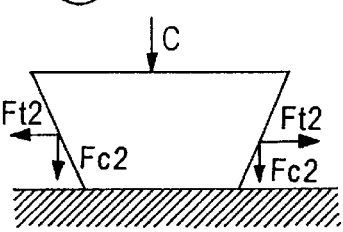

In these configurations, the buckling phenomenon was exacerbated along with the associated undesirable effects, particularly off-centering of the lens, an increased risk of a secondary cataract generated by poor contact between the lens and the posterior capsule, a refraction error by defocusing in the case of nonposterior projection, a reduction in the sensitivity to contrast (loss of resolution) by astigmatic deformation of the optic. Prior Art included haptic portion shapes in which the side segments are radial. In this case, the haptic portions will deform outside the plane of the lens. Another solution is described in French Patent Application FR 2766 699, previously commented upon with reference to FIGS. 4 and 5a. However for these lenses, the transmission of forces from the haptic portions to the optic during projection may be accompanied by astigmatic deformation of the optic. Similarly, in the deformed position, the lens has very low resistance to radial forces, and a small pressure is sufficient to increase the projection, increase the instability phenomenon and reduce self-centering capabilities.

Projection phenomena are accentuated if the sac is retracted.

Figure 1:
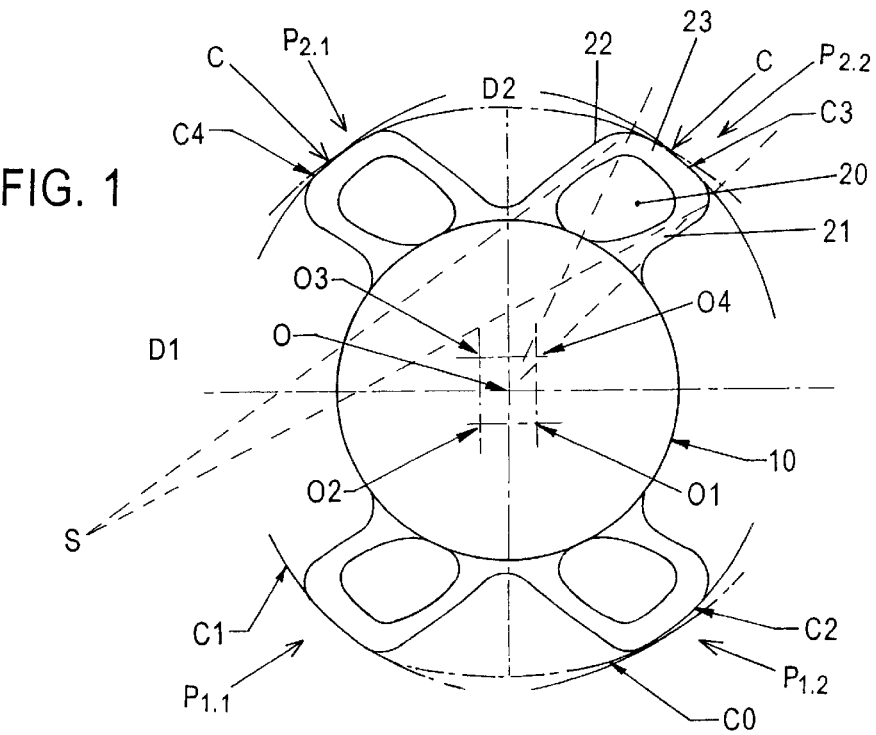
FIGS. 1 and 1a are front views of the intraocular lens according to embodiments of the present invention before insertion in the capsular sac.
Figure 2:
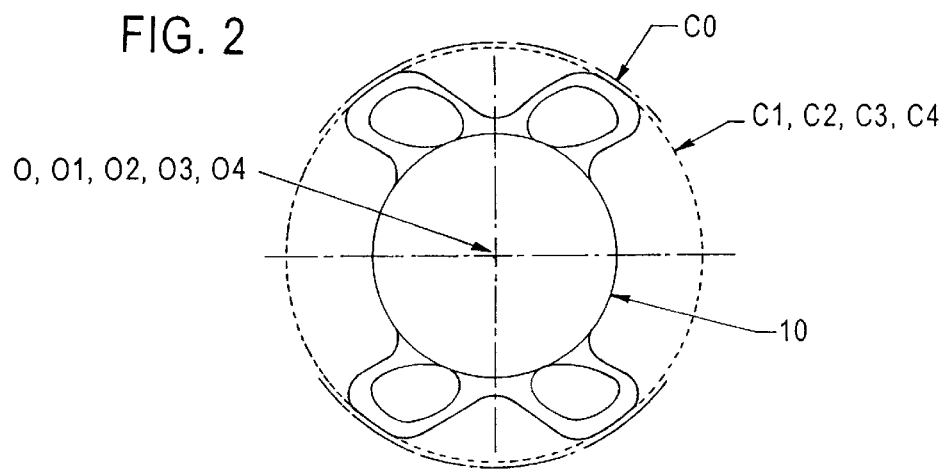
FIG. 2 is a front view of the intraocular lens according to an embodiment of the present invention under stress after insertion in the capsular sac.
Figure 3:
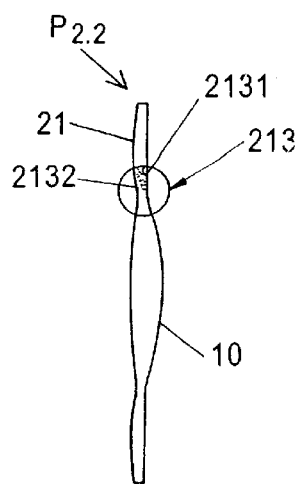
FIG. 3 is a side view of the intraocular lens according to an embodiment of the present invention.

We will now describe the invention with reference to FIGS. 1 to 3. For example, the lens shown in FIGS. 1 to 3 is of the flexible single piece lens type.

In a known manner, the intraocular lens comprises an approximately circular optical part 10, and support parts or haptic portions P1__1, P1.2, P2.2 fixed to the periphery of the optical part 10. There are two pairs of haptic portions P1.1, P1.2, and P2.1, P2.2, each pair being symmetric about a first diameter D1 of the optical part 10. Similarly, the first haptic portion in a pair of haptic portions is symmetric with the second haptic portion in the same pair about a second diameter D2 of the optical part 10. According to the invention, the first diameter D1 and second diameter D2 are perpendicular. Each haptic portion P1.1, P1.2, P2.1, P2.2 comprises a first arm or side segment 21 and a second arm or side segment 22, the first end of which is fixed to the periphery of the optical part 10.

According to a first alternative of the invention, the longitudinal axes of the side segments 21, 22 of each haptic portion 20 intersect at a point S and are not radial with respect to the optical center 0 of the lens. The intersection point S between the two side segments 21, 22 of each haptic portion 20 is outside the angular sector for which the center is coincident with the optical center 0 of the optical part 10, and in which the arc is composed of a contact portion 23 joining the two ends of the side segments 21, 22 of the same haptic portion 20. It should be understood that the angular sector, as defined, extends in the direction of the haptic portion 20 for which the contact portion 23 is used as an arc to the angular sector, but also in the opposite direction. This aspect may also be translated by the fact that for each haptic portion P1.1, P1.a, P2.1, P2.2, the longitudinal axis of a side segment 21, 22 of this haptic portion 20 is inclined on the same side from its radial as the longitudinal axis of the other side segment of the haptic portion with respect to its radial, the radial of a side segment being defined as the axis passing through the second end of each side segment 21, 22 and the optical center 0.

Figure 6A:
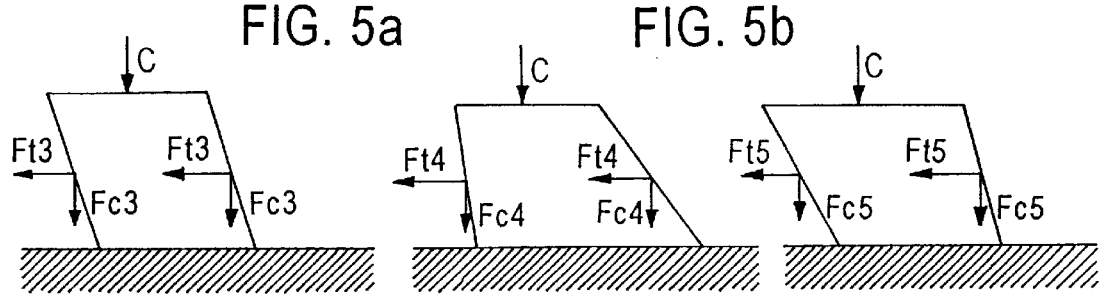
Figure 6B:
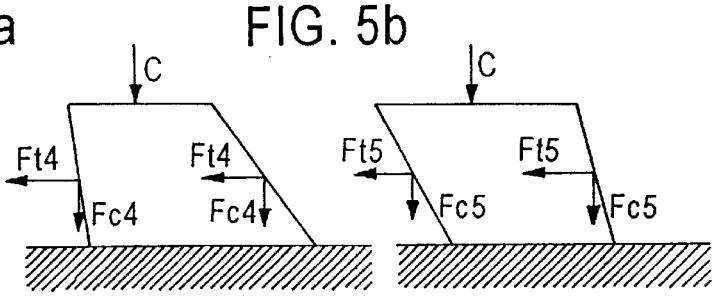
Figure 6C:
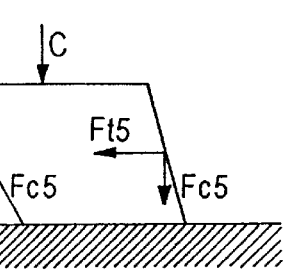

These particular configurations enable bending of the haptic portions P1.1, P1.2, P2.1, P2.a in the plane of the optical part 10 without causing any accumulation of stresses. When the lens is in position in the capsular sac, the haptic portions bear on the inner tissues of the capsular sac and mechanical compression stresses are then applied to them. Under the action of these stresses and considering the configuration of the side segments 21, 22, a rotation moment in the same direction will be applied to each side segment of each haptic portion such that the side segments in the same haptic portion will pivot in the same direction and will cause bending of the haptic portion in the plane of the optical part 10. In this manner, all mechanical stresses will be released by bending of the haptic portions. Thus, forces from the haptic portions will be applied uniformly on the tissues and will hold the lens in the required position. Similarly, bending of the haptic portions causes minimum mechanical deformations to the optical part 10. This is illustrated in FIGS. 6a to 6c in which several different haptic portion geometries can be seen diagrammatically. In these figures, the longitudinal axes of the side segments are inclined on the same side as the radial of each. The compression C acting on each haptic portion P1.1, P1.2, P2.1, P2.2 when the lens is in position generates a haptic portion 20 on each side segment 21, 22 as in Prior Art, causing a centripetal component Fc3, Fc4, Fc5 and a tangential component Ft3, Ft4, Ft5. However, due to the particular geometry of the haptic portions according to the invention, the tangential components Ft3, Ft4, Ft5 are oriented in the same direction which will cause bending of the haptic portion in the plane of the optical part 10.

As the inclination between the haptic portions and the radii of the optical part 10 increases, the bending amplitude also increases but the resistance of the side segments reduces. A large amplitude can compensate for large variations in the diameter between the rest position at which the lens is outside the capsular sac and a working position in which the lens is inserted in the capsular sac.

Figure 1A:
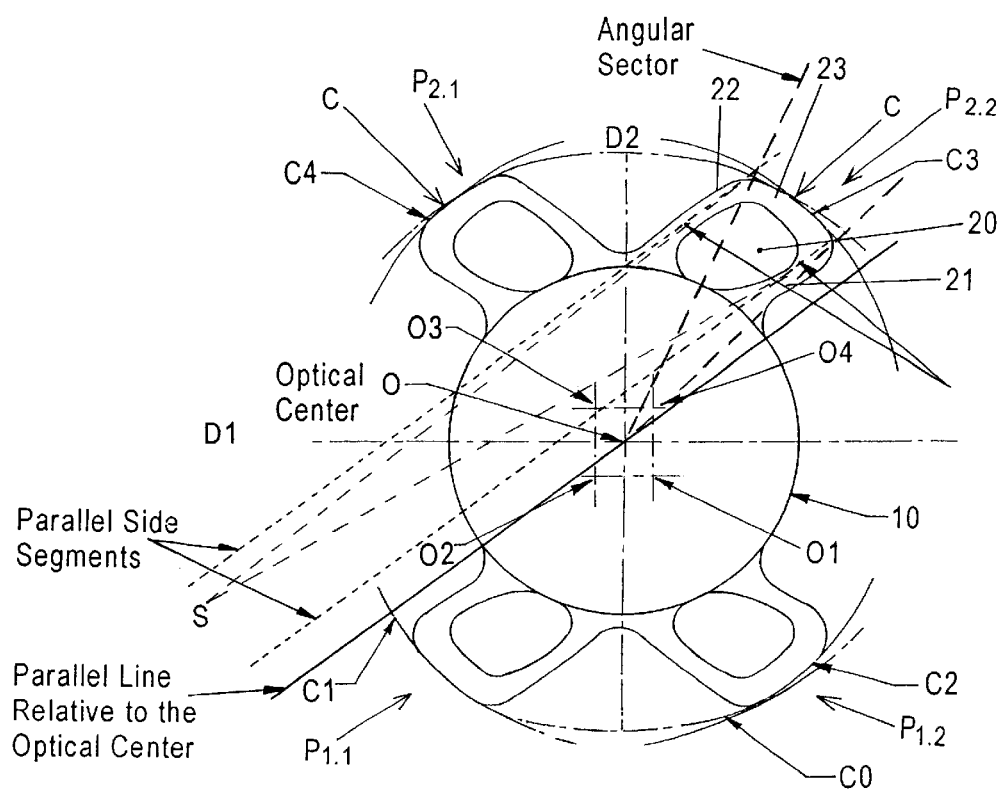

According to another alternative embodiment (see FIG. 1a), the longitudinal axes of the side segments 21, 22 of each haptic portion are parallel. In this case, the axis passing through the optical center parallel to the axes of the side segments 21, 22, in other words corresponding to the axis of the side segments with respect to the optical center 0, must be located outside the angular sector with center 0 and with an arc corresponding to the contact portion 23.

Note that this definition may be applied to the alternative embodiment in which the longitudinal axes of the side segments 21, 22 intersect. If the intersection point S between the two side segments 21, 22 on each haptic portion 20 is to be located outside the angular sector defined above, it is necessary that the longitudinal axes of the side segments 21, 22 with respect to the optical center 0 should not be inside the angular sector.

As described above, this can be geometrically represented by the fact that the longitudinal axes of the side segments 21, 22 of a haptic portion 20 must be inclined in the same direction from their radials, the radial being defined as described above.

The second ends of the side segments 21, 22 of each haptic portion are connected by a support portion 23 or contact zone that provides the contact between the haptic portions P1.1, P1.2, P2.1, P2.2 and the tissues of the capsular sac after the lens has been inserted. According to the invention, each contact zone 23 is inscribed in a circle C1 to C4 with center 01 to 04 not coincident with the optical center 0. The centers of the circles C1 to C4 called the eccentricity circles, inside which the contact zones are inscribed, are located in the optical part. In one alternative embodiment, the centers 01 to 04 of the circles C1 to C4 are symmetric in pairs either about a first diameter D1 or about a second diameter D2, or with respect to the optical center 0. This characteristic gives better lateral stability of the lens, and better self-centering.

When the haptic portions bend while the lens is being inserted, the centers O1' to O4 of the eccentricity circles C1 to C4 will be displaced until they are coincident with or at least as close as possible to the optical center 0. In other words, after the lens according to the present invention has been put into place, the circles C1 to C4 are approximately coincident with a circle CO defining the limits of the capsular sac.

Similarly, the configuration of the side segments 21, 22 of the haptic portions as defined above, induces a difference in the length of the side segments 21, 22. Consequently when bending occurs, the forces due to bending will be greater along the shortest side segment 21. Using a contact zone eccentric from the optical center O, the bending force is balanced on the two side segments 21, 22. The eccentricity of the contact zone 23 depends on the inclination of the haptic portion. As the inclination I of the haptic portions increases, the eccentricity, in other words the distance between the optical center 0 and the center of/the circle C2 tangent to the contact zone 23 increases, and forces will be increasingly transferred to the longest side segment 22.

In order to compensate for the bending resistance of the shortest side segment by increasing its resistance, the cross-sectional area of the shortest side segment 21 is larger than the cross-sectional area of the longest side segment 22.

According to one alternative embodiment, the crosssectional area of the side segments is approximately rectangular with rounded corners.

When inserting the lens in which the contact zones of the haptic portions P1.1, P1.2. P2.1. P2.2 are eccentric, bending of the haptic portions and therefore the side segments 21, 22 causes centering of the circles Cl to C4 on which the contact zones are inscribed onto the circle CO with optical center 0. Thus, after the lens has been inserted into the capsular sac, the entire length of each contact zone 23 is in close contact with the peripheral tissues, which causes a redistribution of the forces and therefore reduces the risk of post-operational complication.

FIG. 3 shows an alternative embodiment of the invention. According to this alternative, the junction 213 between the first end of each side segment 21, 22 and the periphery of the optical part 10 is of a defined shape to prevent the lens from projecting forwards when it is being inserted into the capsular sac. Projection means displacement of the optical part along the optical axis and inclination of the haptic portions with respect to the plane of the optical part 10. According to the invention, the cross-sectional area or profile of the junction 213 is asymmetric with respect to a plane perpendicular to the optical axis of the lens. Thus, according to the invention, the face 2131 of the junction 213 located along the extension of the front face of the optical part 10 is approximately perpendicular to the optical axis. The face 2132 of the junction 213 along the extension of the back face of the optical part 10 forms a defined angle with the face 2131 of the junction 213 located along the extension of the front face such that the part of the junction 213 adjacent to the optical part 10 is narrower than the junction part 213 opposite the optical part 10. Thus, it can be understood that taking account of this angle, backwards projection of the optical part 10 is preferred to forward projection.

According to another alternative, backwards projection can also be amplified by including the plane containing the haptic portion from the optical plane.

FIGS 1 to 4 show a flexible single piece lens. However, the principle of the invention that has just been described can be transposed to rigid intraocular lenses. Thus, for a rigid intraocular lens, the haptic portions will be transferred to the periphery of the lens at locations provided for this purpose.

Thus, the intraocular lens according to the invention is characterized in that each haptic portion P1.1, P1.2, P2.1, P2.2 comprises two arms 21, 22 or side segments, in which a first end is fixed to the periphery of the optical part 10, and for each haptic portion P1.1, P1.2. P2.1. P2.2. the longitudinal axes of the side segments 21, 22 intersect at a point S that is not within an angular sector with a center that is coincident with the optical center 0 of the optical part 10 and the arc of which is composed of a contact portion 23 joining the second ends of the side segments of the same haptic portion.

In another embodiment, each haptic portion P1.1, P1.2, P2.1, P2.2 comprises two arms 21, 22 or side segments, a first end of which is fixed on the periphery of the optical part 10, and for each haptic portion P1.1, P1.2. P2.1, P2.2, tile longitudinal axes of the side segments 21, 22 are parallel, and the longitudinal axes of the side segments 21, 22 are not included in an angular sector with a center coincident with the optical center 0 of the optical part 10, and the arc of which is composed of a contact portion 23 joining the second ends of the side segments of the same haptic portion.

In another embodiment, the second ends of the side segments 21, 22 of each haptic portion are connected through a contact portion 23 or contact zone inscribed in or tangent to a circle C1 to C4 not concentric with the optical center 0 of the optical part 10.

In another embodiment, for each haptic portion, the cross-sectional area of the shortest side segment 21 is greater than the cross-sectional area of the longest side segment 22.

In another embodiment, the cross-sectional areas of the side segments 21, 22 are rectangular with rounded corners.

In another embodiment, the junction 213 between each side segment 21, 22 of each haptic portion P1.1, P1.2, P2.1, P2.2 is provided with an asymmetric longitudinal profile.

In another embodiment, the junction 213 between each side segment 21, 22 of each haptic portion P1.1, P1.2 , P2.1, P2.2 is located in a plane forming a defined angle with the plane of the optical part 10.

In another embodiment, the back face 2131 of the junction is located in a plane perpendicular to the optical axis and the front face 2132 of the junction 213 is included in a plane forming an acute angle with the optical axis such that backwards projection of the optical part is preferred.

In another embodiment, the intraocular lens is a single piece lens and it is made from a flexible material.

In another embodiment, the intraocular lens of the rigid type, the optical part being rigid and the haptic portions (P1.1, P1.2, P2.1, P2.2) being flexible and added onto or machined around the periphery of the optical part.

It will be obvious for persons skilled in the art that this invention could be used with many other forms of specific embodiments without going outside the scope of the invention as claimed. Consequently, these embodiments must be considered simply as illustrations, but can be modified within the field defined by the scope of the attached claims.

What is claimed is:

1. An intraocular lens comprising:
   a substantially disk-shaped optical portion;
   a support portion having two closed pairs of haptic portions arranged symmetrically about a first diameter of said optical portion, each pair of said haptic portions being symmetrical with each other about a second diameter of said optical portion, said second diameter of said optical portion being substantially perpendicular to said first diameter of said optical portion;

each haptic portion having two side segments, each of said side segments having a first end fixed to a periphery of said optical portion and a second end fixed to a contact portion joining said two side segments;

wherein, for each haptic portion, two longitudinal axes defined by said side segments intersect at a point located outside of an angular sector defined by two half-lines having a common vertex and merged with an optical center of said optical portion and passing through said second ends of said side segments of said same haptic portion.

2. The intraocular lens of claim 1, wherein each contact portion is one of either inscribed within or tangent to a circle having a center displaced from said optical center of said optical portion.

3. The intraocular lens of claim 1, wherein, for each haptic portion, a cross-sectional area of a shortest side segment is greater than a cross-sectional area of a longest side segment.

4. The intraocular lens of claim 3, wherein said cross-sectional areas of said side segments are rectangular with rounded corners.

5. The intraocular lens of claim 1, further comprising a junction located between each side segment of each haptic portion, each junction having an asymmetric longitudinal profile.

6. The intraocular lens of claim 1, further comprising a junction located between each side segment of each haptic portion, each junction located in a plane forming a defined angle with a plane of said optical portion.

7. The intraocular lens of claim 1, further comprising a junction located between each side segment of each haptic portion, a back face of each junction located in a plane perpendicular to an optical axis of said lens and a front face of said junction included in a plane forming an acute angle with said optical axis to facilitate backwards projection of said optical portion.

8. The intraocular lens of claim 1, wherein said lens comprises a unitary lens of a flexible material.

9. The intraocular lens of claim 1, wherein said optical portion is rigid and said haptic portions are flexible and are located around said periphery of said optical portion.

10. An intraocular lens comprising:

a substantially disk-shaped optical portion;

a support portion having two closed pairs of haptic portions arranged symmetrically about a first diameter of said optical portion, each pair of said haptic portions being symmetrical with each other about a second diameter of said optical portion, said second diameter of said optical portion being substantially perpendicular to said first diameter of said optical portion;

each haptic portion having two side segments of different lengths, each of said side segments having a first end fixed to a periphery of said optical portion and a second end fixed to a contact portion joining said two side segments;

wherein, for each haptic portion, two longitudinal axes defined by said side segments are parallel to each other and an axis passing through an optical center of said optical portion and parallel to said longitudinal axes of said side segments is located outside of an angular sector defined by two half-lines having a common vertex and merged with said optical center of said optical portion and passing through said second ends of said side segments of said same haptic portion.

11. The intraocular lens of claim 10, wherein each contact portion is one of either inscribed within or tangent to a circle having a center displaced from said optical center of said optical portion.

12. The intraocular lens of claim 10, wherein, for each haptic portion, the cross-sectional area of the shorter side segment is greater than the cross-sectional area of the longer side segment.

13. The intraocular lens of claim 12, wherein said cross-sectional areas of said side segments are rectangular with rounded corners.

14. The intraocular lens of claim 10, further comprising a junction located between each side segment of each haptic portion, each junction having an asymmetric longitudinal profile.

15. The intraocular lens of claim 10, further comprising a junction located between each side segment of each haptic portion, each junction located in a plane forming a defined angle with a plane of said optical portion.

16. The intraocular lens of claim 10, further comprising a junction located between each side segment of each haptic portion, a back face of each junction located in a plane perpendicular to an optical axis of said lens and a front face of said junction included in a plane forming an acute angle with said optical axis to facilitate backwards projection of said optical portion.

17. The intraocular lens of claim 10, wherein said lens comprises a unitary lens of a flexible material.

18. The intraocular lens of claim 10, wherein said optical portion is rigid and said haptic portions are flexible and are located around said periphery of said optical portion.

* * * * *

UNITED STATES PATENT AND TRADEMARK OFFICE
CERTIFICATE OF CORRECTION

PATENT NO. : 6,755,860 B2
DATED : June 29, 2004
INVENTOR(S) : Renato Liffredo et al.

It is certified that error appears in the above-identified patent and that said Letters Patent is hereby corrected as shown below:

<u>Title page,</u>
Item [75], should read:
-- Inventors:    Renato Liffredo, Parablago (IT)
                 Denis Delage, Yevre le Chatel (FR) --.

Signed and Sealed this

Seventeenth Day of January, 2006

JON W. DUDAS
*Director of the United States Patent and Trademark Office*